United States Patent [19]

Fujimaru et al.

[11] Patent Number: 6,110,984
[45] Date of Patent: Aug. 29, 2000

[54] WATER-SWELLABLE CROSSLINKED POLYMER, PRODUCTION PROCESS THEREFOR, AND MEASUREMENT METHOD FOR PORE VOLUME OF SWOLLEN CROSSLINKED POLYMER

[75] Inventors: Hirotama Fujimaru; Koichi Yonemura, both of Himeji; Nobuyuki Harada, Suita, all of Japan

[73] Assignee: Nippon Shokubai Co., Ltd., Osaka, Japan

[21] Appl. No.: 08/946,452

[22] Filed: Oct. 7, 1997

[30] Foreign Application Priority Data

Oct. 14, 1996 [JP] Japan ..................................... 8-270949

[51] Int. Cl.⁷ ....................................................... C08J 9/28
[52] U.S. Cl. ................................................. 521/64; 521/72
[58] Field of Search .......................................... 521/64, 72

[56] References Cited

U.S. PATENT DOCUMENTS

| | | |
|---|---|---|
| 4,415,388 | 11/1983 | Korpman ................................. 425/208 |
| 4,529,739 | 7/1985 | Scott et al. ................................ 521/72 |
| 4,734,478 | 3/1988 | Tsubakimoto et al. . |
| 4,808,637 | 2/1989 | Boardman et al. ..................... 521/50.5 |
| 5,314,420 | 5/1994 | Smith et al. . |
| 5,328,935 | 7/1994 | Van Phan et al. . |
| 5,338,766 | 8/1994 | Phan et al. ................................ 521/64 |

FOREIGN PATENT DOCUMENTS

| | | |
|---|---|---|
| 43 44 224 A1 | 6/1995 | Germany . |
| 61-16903 | 1/1986 | Japan . |
| 2 162 525 | 2/1986 | United Kingdom . |

*Primary Examiner*—Morton Foelak

[57] ABSTRACT

The present invention provides a water-swellable crosslinked polymer that displays high absorption capacity when put under an increased pressure in a state combined with a fibrous base matter. The water-swellable crosslinked polymer has a total pore volume of 60 v/v % or more relative to the entire amount of the absorption of a physiological salt solution into the polymer with regard to pores with a pore size of 51–270 Å when swollen with the physiological salt solution, or the polymer has a total pore volume of 80 v/v % or more relative to the entire amount of the absorption of ion-exchanged water into the polymer with regard to pores with a pore size of 51–270 Å when swollen with the ion-exchanged water.

18 Claims, No Drawings

WATER-SWELLABLE CROSSLINKED POLYMER, PRODUCTION PROCESS THEREFOR, AND MEASUREMENT METHOD FOR PORE VOLUME OF SWOLLEN CROSSLINKED POLYMER

BACKGROUND OF THE INVENTION

A. Technical Field

The present invention relates to: a water-swellable crosslinked polymer, which is excellent in absorption capacity under an increased pressure; a production process for this polymer; and a measurement method for a pore volume of a swollen crosslinked polymer.

B. Background Art

In recent years, high water-absorbent resins with a high degree of water absorbency have been developed and are in practical use as disposable diapers, sanitary napkins, and so on by combining the high water-absorbent resins with fibrous base matters such as cotton, pulp, paper, and sponge.

However, these high water-absorbent resins have problems in that even if they display high absorption capacity by themselves, they do not necessarily display high absorption capacity when actually used as disposable diapers and so on. That is to say, when actually used, the resins are put under an increased pressure in a state combined with fibrous matters, so factors other than absorption by the resins alone give affections.

A method for enhancing the absorption capacity under an increased pressure is disclosed in Japanese Patent Application Publication (Kokai) No. 61-16903 and so on. In actual circumstances, however, this method is still not sufficient.

SUMMARY OF THE INVENTION

A. Object of the Invention

An object of the present invention is to provide a water-swellable crosslinked polymer, which displays sufficiently high absorption capacity when put under an increased pressure in a state combined with fibrous matters, and a production process for this polymer, and to provide a measurement method by which the pore volume of pores with a specific range of size in a swellable crosslinked polymer as swollen with a solvent can precisely be measured with ease.

B. Disclosure of the Invention

The present inventors paid attention to pore sizes of a water-swellable crosslinked polymer in order to solve the above-mentioned problems, and found that the ratio of pores which have an intermediate pore size of 51–270 Å when the polymer is swollen with a physiological salt solution or ion-exchanged water is important, and that it is important that the average pore size and the standard deviation in pore size are in the specific ranges respectively when the polymer is swollen with ion-exchanged water, and the inventors further found a method for measuring a pore volume of pores with a specific range of size.

A water-swellable crosslinked polymer, according to the present invention, has a total pore volume of 60 v/v % or more relative to the entire amount of the absorption of a physiological salt solution into the polymer with regard to pores with a pore size of 51–270 Å when the polymer is swollen with the physiological salt solution.

In addition, a water-swellable crosslinked polymer, according to the present invention, has PV (51–270 Å) of 60 v/v % or more relative to the entire amount of the absorption of a physiological salt solution into the polymer, wherein the PV (51–270 Å) is defined by a method comprising the following steps of:

A. allowing a water-swellable crosslinked polymer (W1 g), which stands in an equilibrium state swollen with a physiological salt solution (W2 ml), to fall again into an equilibrium state by adding a physiological salt solution (W3 ml, concentration Ci %) of a thread-ball-shaped molecule with molecular diameter R to the polymer; and then filtering off the polymer as swollen with the physiological salt solution; and then measuring concentration Cf % of the thread-ball-shaped molecule in the resultant filtrate;

B. defining PV (0–R) (ml/g) as PV (0–R) (ml/g)=(W2+W3)[1−{W3/(W2+W3)}×(Ci/Cf)]/W1;

C. determining PV (0–51 Å) and PV (0–270 Å) using a thread-ball-shaped molecule with R of 51 Å and a thread-ball-shaped molecule with R of 270 Å; and D. defining PV (51–270 Å) as PV (51–270 Å)=PV (0–270 Å)−PV (0–51 Å).

In addition, a water-swellable crosslinked polymer, according to the present invention, has a total pore volume of 80 v/v % or more relative to the entire amount of the absorption of ion-exchanged water into the polymer with regard to pores with a pore size of 51–270 Å when the polymer is swollen with the ion-exchanged water.

In addition, a water-swellable crosslinked polymer, according to the present invention, has PVW (51–270 Å) of 80 v/v % or more relative to the entire amount of the absorption of ion-exchanged water into the polymer, wherein the PVW (51–270 Å) is defined by a method comprising the following steps of:

E. allowing a water-swellable crosslinked polymer (W1 g), which stands in an equilibrium state swollen with ion-exchanged water (W4 ml), to fall again into an equilibrium state by adding an ion-exchanged water solution (W5 ml, concentration Ci %) of a thread-ball-shaped molecule with molecular diameter R to the polymer; and then filtering off the polymer as swollen with the ion-exchanged water; and then measuring concentration Cf % of the thread-ball-shaped molecule in the resultant filtrate;

F. defining PVW (0–R) (ml/g) as PVW (0–R) (ml/g)= (W4+W5)[1−{W5/(W4+W5)}×(Ci/Cf)]/W1;

G. determining PVW (0–51 Å) and PVW (0–270 Å) using a thread-ball-shaped molecule with R of 51 Å and a thread-ball-shaped molecule with R of 270 Å; and H. defining PVW (51–270 Å) as PVW (51–270 Å) PVW (0–270 Å)−PVW (0–51 Å).

In addition, a water-swellable crosslinked polymer, according to the present invention, has an average pore size of 100–300 Å and a standard deviation of 115 or less in pore size when the polymer is swollen with ion-exchanged water.

In addition, a water-swellable crosslinked polymer, according to the present invention, has an average pore size of 100–300 Å and a standard deviation of 115 or less in pore size, wherein the average pore size is defined by a method comprising the following steps of:

I. allowing a water-swellable crosslinked polymer (W1 g), which stands in an equilibrium state swollen with ion-exchanged water (W4 ml), to fall again into an equilibrium state by adding an ion-exchanged water solution (W5 ml, concentration Ci %) of a thread-ball-shaped molecule with molecular diameter R to the polymer; and then filtering off the polymer as swollen with the ion-exchanged water; and then measuring concentration Cf % of the thread-ball-shaped molecule in the resultant filtrate;

J. defining PVW (0–R) (ml/g) as PVW (0–R) (ml/g)= (W4+W5)[1−{W5/(W4+W5)}×(Ci/Cf)]/W1;

K. determining PVW (0–51 Å), PVW (51–90 Å), PVW (90–118 Å), PVW (118–270 Å), PVW (270–560 Å), and PVW (0–560 Å) using a thread-ball-shaped molecule with R of 51 Å, a thread-ball-shaped molecule with R of 90 Å, a thread-ball-shaped molecule with R of 118 Å, a thread-ball-shaped molecule with R of 270 Å, and a thread-ball-shaped molecule with R of 560 Å; and L. defining the average pore size as:

$$\text{average pore size} = [25.5 \times \text{PVW (0–51 Å)} \\ + 70.5 \times \text{PVW (51–90 Å)} \\ + 104 \times \text{PVW (90–118 Å)} \\ + 194 \times \text{PVW (118–270 Å)} \\ + 415 \times \text{PVW (270–560 Å)}] / \\ [\text{PVW (0–560 Å)}].$$

A process for producing a water-swellable crosslinked polymer, according to the present invention, comprises the step of subjecting a hydrophilic high molecule to a crosslinking reaction in an aqueous solution, wherein the crosslinking reaction is carried out in such a manner that the change in the concentration of a solid content falls within the range of ±30%.

In addition, a process for producing a water-swellable crosslinked polymer, according to the present invention, comprises the step of subjecting a hydrophilic high molecule to a crosslinking reaction in an aqueous solution, wherein the crosslinking reaction is carried out in such a manner that the concentration of a solid content falls within the range of 2 to 40%.

In these production processes, it is preferable that the hydrophilic high molecule has a weight-average molecular weight of 1,000,000 or more before crosslinked, or that the hydrophilic high molecule is a partially neutralized polyacrylic acid before crosslinked.

A method for measuring a pore volume of pores with a specific range of size in a swellable crosslinked polymer as swollen with a solvent, according to the present invention, comprises the steps of:

allowing a swellable crosslinked polymer (W1 g), which stands in an equilibrium state swollen with solvent S (W2 ml), to fall again into an equilibrium state by adding a solvent S solution (W3 ml, concentration Ci %) of a thread-ball-shaped molecule with molecular diameter R to the polymer; and then filtering off the polymer as swollen with solvent S; and then measuring concentration Cf % of the thread-ball-shaped molecule in the resultant filtrate; and thereby determining volume PV (0–R) of solvent S, as absorbed into pores having a size of 0–R in a state swollen with solvent S, from the following equation:

$$PV(0-R)(ml/g)=(W2+W3)[1-\{W3/(W2+W3)\}\times(Ci/Cf)]/W1.$$

These and other objects and the advantages of the present invention will be more fully apparent from the following detailed disclosure.

DETAILED DESCRIPTION OF THE INVENTION

First, an explanation is made about the present invention method for measuring a pore volume of pores with a specific range of size in a swellable crosslinked polymer as swollen with a solvent.

The "pore size," referred to herein, is a diameter of an imaginary sphere that can enter a space as formed by a crosslinked high molecule composing a gel.

W1 g of a swellable crosslinked polymer, which stands in an equilibrium state swollen with solvent S (W2 ml), is allowed to fall again into an equilibrium state by adding a solvent S solution (W3 ml, concentration Ci %) of a thread-ball-shaped molecule with molecular diameter R to the polymer, and then the polymer as swollen with solvent S is filtered off, and then concentration Cf % of the thread-ball-shaped molecule in the resultant filtrate is measured.

Because the diameter of the thread-ball-shaped molecule is R, the thread-ball-shaped molecule can enter pores with a size of larger than R, among pores of the swollen crosslinked polymer, while the thread-ball-shaped molecule cannot enter pores with a size of smaller than R. In pores (0–R) smaller than R, therefore, the thread-ball-shaped molecule is not present, and only solvent S is absorbed.

Thus, if the volume of solvent S, as absorbed into pores having a size of 0–R in a state swollen with solvent S, is defined as PV (0–R) (ml/g), then a relation between W1, W2, W3, Ci, and Cf above is represented by $$Ci \cdot W3 = Cf(W2+W3-W1 \times PV)$$

because the amount of the thread-ball-shaped molecule in the solution of the thread-ball-shaped molecule is the same as the amount of the thread-ball-shaped molecule in the system standing in an equilibrium state, and PV (0–R) (ml/g) is therefore represented by the following equation:

$$PV(0-R)(ml/g)=(W2+W3)[1-\{W3/(W2+W3)\}\times(Ci/Cf)]/W1.$$

This PV (0–R) (ml/g) is defined as the "total pore volume of pores having a pore size of 0–R when swollen with solvent S."

If two types of R1 and R2 (R1<R2) are used as diameter R of the thread-ball-shaped molecule, PV (0–R1) and PV (0–R2) can be measured respectively, and PV (R1–R2) can be determined from $$PV(R1-R2)=PV(0-R2)-PV(0-R1).$$

Examples of usable solvents include super pure water, a physiological salt solution (0.9 wt % aqueous sodium chloride solution), and ion-exchanged water, but the solvent is not limited to them. As to the thread-ball-shaped molecule, dextran (for example, made by Pharmacia Biotech Co., Ltd.) can be used.

The water-swellable crosslinked polymer, according to the present invention, has many pores and is characterized in that when swollen with a physiological salt solution, the polymer has a total pore volume, PV (51–270 Å) (ml/g), of 60 v/v % or more relative to the entire amount of the absorption of the physiological salt solution into the polymer with regard to pores with a pore size of 51–270 Å. In addition, the water-swellable crosslinked polymer, according to the present invention, is characterized in that when swollen with ion-exchanged water, the polymer has a total pore volume, PVW (51–270 Å) (ml/g), of 80 v/v % or more relative to the entire amount of the absorption of the ion-exchanged water into the polymer with regard to pores with a pore size of 51–270 Å.

Such a total pore volume can be measured with a physiological salt solution or ion-exchanged water if the measurement method of the present invention is carried out, in which a physiological salt solution or ion-exchanged water is used as solvent S, and dextran of 51 Å (for example, "Dextran T10," made by Pharmacia Biotech Co., Ltd.) and dextran of 270 Å (for example, "Dextran T500," made by Pharmacia Biotech Co., Ltd.) are used as the thread-ball-shaped molecules. PV (51–270 Å) is defined as PV (51–270 Å)=PV (0–270 Å)–PV (0–51 Å), and PVW (51–270 Å) is defined as PVW (51–270 Å)=PVW (0–270 Å)–PVW (0–51 Å). In addition, the entire amount of the absorption of the physiological salt solution or ion-exchanged water into the water-swellable crosslinked polymer can be determined by measuring PV (0–560 Å) using dextran of 560 Å (for example, "Dextran T2000," made by Pharmacia Biotech Co., Ltd.), because it is considered that the water-swellable crosslinked polymer has substantially no pore that is larger than 560 Å.

PV (51–270 Å) needs to be 60 v/v % or more relative to the entire amount of the absorption of the physiological salt solution into the water-swellable crosslinked polymer, but preferable PV (51–270 Å) is 80 v/v % or more. PVW (51–270 Å) needs to be 80 v/v % or more relative to the entire amount of the absorption of ion-exchanged water into the water-swellable crosslinked polymer, but preferable PVW (51–270 Å) is 85 v/v % or more. The higher the PV (51–270 Å) and PVW (51–270 Å) are, the more excellent the absorption capacity under an increased pressure in a state combined with a fibrous base matter is.

In addition, the water-swellable crosslinked polymer, according to the present invention, is characterized in that when swollen with ion-exchanged water, the polymer has an average pore size of 100–300 Å and a standard deviation of 115 or less in pore size. The average pore size can be measured by carrying out the aforementioned measurement method, in which: PVW (0–51 Å), PVW (51–90 Å), PVW (90–118 Å), PVW (118–270 Å), and PVW (270–560 Å) are determined using thread-ball-shaped molecules with diameters of 51 Å, 90 Å, 118 Å, 270 Å, and 560 Å respectively (for example, "Dextran T10, T40, T70, T500, T2000," made by Pharmacia Biotech Co., Ltd.); the respective pore volumes in those pore size ranges are assumed to be respective intermediate values (25.5, 70.5, 104, 194, 415) of those ranges; and the average pore size is calculated in accordance with the below-mentioned equation. On the basis of the resultant average value, the standard deviation in pore size is also calculated.

Average pore size = [25.5 × PVW (0–51 Å)
 +70.5 × PVW (51–90 Å)
 +104 × PVW (90–118 Å)
 +194 × PVW (118–270 Å)
 +415 × PVW (270–560 Å)]/
 [PVW (0–560 Å)]

The average pore size needs to be in the range of 100 to 300 Å, but a preferable one is in the range of 150 to 250 Å. The standard deviation in pore size needs to be 115 or less, but it is preferably 110 or less, more preferably, 105 or less.

That is to say, the present inventors found that it is important for the absorption capacity under an increased pressure that the ratio of pores with an intermediate pore size of 51–270 Å is large, in other words, the average pore size is in the range of 100 to 300 Å and the pore size distribution is sharp. Although not clear, a principle thereof can be explained as follows:

As to a water-swellable crosslinked polymer with a certain chemical composition, it is known that as the crosslinking density becomes higher, the gel volume decreases, and that as the crosslinking density becomes lower, the gel volume increases. In other words, it is considered that if the distance between crosslinked sites of a gel is long, namely, if pores of a gel is large, a space holding an absorbed solution is large, so the absorption capacity can be enhanced.

On the other hand, the swelling and the shrinkage of a water-swellable crosslinked polymer can be explained referring to an osmotic pressure between inside and outside of a gel, and the osmotic pressure is defined as the sum of the below-mentioned four pressures in accordance with the following Flory-Huggins equation:

Osmotic pressure of gel = pressure due to rubber elasticity of high molecules between crosslinked sites
 + pressure due to counter ion in high molecule network
 + pressure due to interaction between high molecule chain and liquid (solubility of high molecule)
 + pressure due to mixing entropy of high molecule network and liquid As to this equation, if attention is paid to the term of the pressure due to the rubber elasticity of the network in which the distance between crosslinked sites participates, pressure $\pi$ due to the rubber elasticity is shown as follows:

$$\pi = \nu kT\{\Phi/\Phi_0 - (\Phi/\Phi_0)^{1/3}\}$$

($\nu$: number of high molecules between crosslinked sites, k: Boltzmann constant, $\Phi$: volume fraction of high molecule chain, $\Phi_0$: volume fraction of high molecule chain having random conformation).

From this equation, it has been considered that as number $\nu$ of the high molecules between crosslinked sites becomes more, namely, as the crosslinked sites becomes more, the osmotic pressure of a gel becomes higher.

From these relations, the present inventors found that: where pores are too large, they have a spatial spread, but the osmotic pressure of a gel is low, and pores shrink under conditions where a mechanical pressure or a pressure of ions in brine is present, so a gel of high absorption capacity under an increased pressure or a saltproof gel cannot be obtained, and further that: where pores are too small, the osmotic pressure of a gel is high, but the spatial spread is small such that a gel of high absorption capacity cannot be obtained.

Thus, the inventors first found the method for measuring a pore volume of pores of the swellable crosslinked polymer, as swollen with a solvent, using the thread-ball-shaped molecule, and measured volumes of pores in various ranges of pore sizes with regard to water-swellable crosslinked polymers. As a result, the inventors found that a water-swellable crosslinked polymer having a large pore volume with regard to pores having a size of 51 to 270 Å in a state swollen with a physiological salt solution or ion-exchanged water or a water-swellable crosslinked polymer having an average pore size of 100 to 300 Å and a sharp pore size distribution displays high absorption capacity under an increased pressure.

In addition, in the present invention, it is important that a pore size in a state swollen with a physiological salt solution or ion-exchanged water is defined as the standard. Even if a pore size in a state swollen with another solvent such as super pure water is defined as the standard, it is impossible to carry out evaluation corresponding to the actual use form.

Such a water-swellable crosslinked polymer of large PV (51–270 Å) or a water-swellable crosslinked polymer having an average pore size of 100 to 300 Å and a sharp pore size distribution, for example, can be obtained by the present invention process for producing a water-swellable crosslinked polymer, but the production process is not limited to this process of the present invention.

The present invention process for producing a water-swellable crosslinked polymer is characterized in that when a hydrophilic high molecule is subjected to a crosslinking reaction in an aqueous solution to produce a water-swellable crosslinked polymer, the crosslinking reaction is carried out in such a manner that the change in the concentration of a solid content falls within the range of ±30%, and/or that the concentration of a solid content falls within the range of 2 to 40%. It is more preferable that the change in the concentration is within the range of ±20%, or that the concentration is within the range of 10 to 30%. Specifically, a process is exemplified in which the crosslinking is carried out with a vessel (e.g. polypropylene cup) capped such that the solvent may not evaporate during the crosslinking reaction. However, there is no especial limitation providing that the process satisfies the above-mentioned conditions with regard to the solid content concentration even if the crosslinking is not carried out under the above-mentioned airtight conditions. The temperature and the period of time for the crosslinking are not especially limited if they complete the crosslinking. Methods for the crosslinking are not especially limited, either.

Conventionally, because the crosslinking was carried out while or after drying the aqueous solution of the hydrophilic high molecule, the change in the solid content concentration was large during the crosslinking reaction, or the crosslinking was carried out under conditions where the solid content concentration was high. Because the spread of a polymer chain greatly depends on the polymer concentration, when the polymer concentration is high, many tangles of the polymer are present, or the shrinkage of the polymer chain occurs. Where the crosslinking is carried out in such a state, the tangles or the shrinkage of the polymer is fixed, and the spatial spread in a gel becomes small, and small networks are therefore exclusively formed, and as a result, the ratio of PV (51–270 Å) becomes low, or the average pore size does not fall within the range of 100 to 300 Å, or even if the average pore size falls within this range the pore size distribution is not sharp.

The higher the weight-average molecular weight of the hydrophilic high molecule before crosslinked is, the higher the water absorption capacity under an increased pressure is. Therefore, the weight-average molecular weight of the hydrophilic high molecule before crosslinked is preferably 1,000,000 or more.

An example of processes for producing the water-swellable crosslinked polymer of large PV (51–270 Å) or the water-swellable crosslinked polymer having an average pore size of 100 to 300 Å and a sharp pore size distribution other than the above-mentioned processes is a process comprising the following steps of: polymerizing a monomer in a nonmetal vessel under nonshearing for a long period of time; dividing the resultant polymer into fine pieces under no shearing with tools such as scissors; and drying the fine pieces at a low temperature. For forming uniform gel pores, it is preferable that the polymerization, pulverization, and drying are carried out in such a gentle manner, for example, it is preferable that: a nonmetal vessel is used as the polymerization vessel, the polymerization is carried out under nonstirring at or below 60° C., and the resultant polymer gel is pulverized under nonshearing. Where the polymerization is carried out under stirring above 60° C. or where the pulverization for dividing the resultant polymer gel into fine pieces is carried out under shearing, networks are unfavorably collapsed.

The hydrophilic high molecule is generally a polymer having a hydrophilic functional group, such as a carboxyl group, a hydroxyl group, an amide group, an amino group, or a sulfonic acid group, on a side chain of the polymer. Examples of the hydrophilic high molecule include: polyacrylic acids as obtained by polymerizing acrylic acid; isobutylene-maleic acid copolymers as obtained by copolymerizing maleic anhydride and isobutylene and then carrying out saponification; polyvinyl alcohols as obtained by polymerizing vinyl acetate and then carrying out saponification; and polyamines as obtained by polymerizing N-vinylic monomers and then carrying out hydrolysis.

Main raw materials of the hydrophilic high molecule in the present invention are not especially limited. Examples thereof include: homopolymers of monomers selected from the group consisting of monovinylic monomers having a carboxyl group, such as crotonic acid, fumaric acid, and maleic anhydride, alkaline metal salts or monovalent amine salts of these vinylic monomers, or copolymers of these monomers with other monomers such as acrylamide, methacrylamide, acrylonitrile, and styrene; and polymers as obtained by hydrolyzing in the presence of an alkali a polymerized product as obtained by polymerizing a major proportion of at least one monomer selected from the group consisting of acrylamide, methacrylamide, acrylonitrile, acrylic esters, and methacrylic esters. In addition, the above-mentioned examples further include polymers as obtained by hydrolyzing in the presence of an acid a polymerized product as obtained by polymerizing a major proportion of at least one monomer selected from the group consisting of N-vinylic monomers such as N-vinylformamide, N-acetoamide, and N-vinylpyrrolidone. Particularly, partially neutralized polyacrylic acids are preferable.

The partially neutralized polyacrylic acid is a polyacrylic acid of which 25–95% of carboxyl groups are salts with monovalent alkaline metals, such as lithium, potassium, and sodium, or salts with ammonia, or salts with monovalent amines such as monoethanolamine. The partially neutralized polyacrylic acid is obtained by copolymerizing acrylic acid and a salt thereof, or by partially neutralizing a polyacrylic acid as formed by polymerizing acrylic acid. Examples of methods for the neutralization include: a method in which the neutralization is carried out when a hydrophilic high molecule of a predetermined concentration is obtained; a method in which the neutralization is carried out when a crosslinking agent is added; and a method in which the neutralization is carried out after the crosslinking is carried out. However, there is no especial limitation in the neutralization method.

A polymerization method for obtaining the hydrophilic high molecule is not especially limited, and generally, the polymerization is carried out using a radical initiator in a solution. However, the polymerization can also carried out in manners such as suspension polymerization, emulsion polymerization, and bulk polymerization. In addition, depending on the types of initiators, cation polymerization, anion polymerization, and ring-opening polymerization can also be carried out besides the radical polymerization.

The crosslinking agent is not especially limited if it can form a crosslinked structure by a reaction that does not involve the elimination of low molecules such as water. Where the hydrophilic high molecule is a polyacrylic acid, examples of the crosslinking agent include those which have a functional group that makes a crosslinking reaction with a carboxyl group without involving any dehydration reaction, such as polyhaloalkanols, haloepoxyalkanes, amphoteric sulfoniums, polyglycidyl ethers, bisphenol-A-epichlorohydrin epoxy resins, and polyamideamine/epichlorohydrin (e.g. Kymene made by Hercules, Inc.).

The amount of the crosslinking agent is preferably in the range of 0.1 to 10% by weight of the solid content of the hydrophilic high molecule. In addition, it is preferable that the crosslinking agent is mixed simultaneously with when an aqueous solution of the hydrophilic high molecule is conditioned so as to have a predetermined concentration.

After the crosslinking reaction has finished, the resultant product is dried, pulverized with a pulverizer, and classified with a sieve, thus obtaining the water-swellable crosslinked polymer. The drying can be carried out in manners such as vacuum drying, hot-air drying, and freeze-drying.

Where the water-swellable crosslinked polymer of the present invention is used as a composite as obtained by combining the polymer with a base material, examples of the base material as used include: spongy porous base matters such as sponge and synthetic resin foams; fibers, such as paper, string, nonwoven fabrics, and woven fabrics, as made of synthetic fibers (e.g. polyesters, polyolefins) or cellulose fibers (e.g. cotton, pulp).

If a solution of a mixture of a monomer, which is capable of forming the hydrophilic high molecule by polymerization, and a crosslinking agent is applied to the base material, and if polymerization is then carried out, a water-absorbent composite in which the resultant polymer is fixed on the base material can be obtained.

(Effects and Advantages of the Invention):

The water-swellable crosslinked polymer, according to the present invention, and a product as obtained by the present invention process for producing a water-swellable crosslinked polymer are both water-swellable crosslinked polymers that display high absorption capacity when put under an increased pressure in a state combined with a fibrous base matter.

The pore volume of pores with a specific range of size in a swellable crosslinked polymer as swollen with a solvent can precisely be measured with ease by the measurement method according to the present invention.

DETAILED DESCRIPTION OF THE PREFERRED EMBODIMENTS

Hereinafter, the present invention is more specifically illustrated by the following examples of some preferred embodiments in comparison with comparative examples not according to the invention. However, the present invention is not limited to the below-mentioned examples.

In the below-mentioned examples, the size distribution of pores in gels of water-absorbent resins in a state swollen with a physiological salt solution or ion-exchanged water and the evaluation as to absorbent articles are measured by the following methods:

(a) Size Distribution of Pores in Gels in a State Swollen with a Physiological Salt Solution:

About 10 mg (W1 g) of a water-swellable crosslinked polymer is precisely weighed out and then swollen by placing it into a screw tube of 100 ml along with about 30 ml (W2 ml) of a physiological salt solution, and then allowed to stand stationary for 60 hours. About 30 ml (W3 ml) of a 1.00% (Ci %) physiological salt solution of dextran with a molecular diameter of 51 Å ("Dextran T10," made by Pharmacia Biotech Co., Ltd.) is added, and the tube is capped and then shaken for 60 hours with a shaker ("Double Shaker" NR-150, made by Taitec Co., Ltd.). After this shaking, the resultant swollen gel is filtered off with a glass filter. The filtrate is subjected to GPC analysis to determine the concentration (Cf %) of dextran in the filtrate from a calibration curve as made beforehand from the peak height of dextran with a known concentration. Conditions for the GPC analysis are as follows:

GPC analyzer: Liquid Chromatograph, made by Waters, Ltd.

Column: "Shodex Asahipak" GF7M-HQ, made by Showa Denko Co., Ltd.

Column temperature: 35° C.

Eluent: $Na_2HPO_4$ (13.8 g), $NaH_2PO_4 \cdot 2H_2O$ (18.46 g), $NaN_3$ (0.04 g), $H_2O$ (1967.7 g)

Flow rate: 0.5 ml/min

Amount of charge: 50 µl

Detector: RI

Pore volume PV (0–51) (ml/g) of pores of 0–51 Å with a physiological salt solution was calculated from the weights W1, W2, and W3, the initial concentration Ci % of the physiological salt solution of dextran, and the concentration Cf % of dextran in the filtrate in accordance with the following equation:

$$PV(0-51)(ml/g)=(W2+W3)[1-\{W3/(W2+W3)\}\times(Ci/Cf)]/W1.$$

Pore volume PV (0–270) (ml/g) of pores of 0–270 Å with a physiological salt solution was measured in the same way as the above-mentioned, except that the dextran with a molecular diameter of 51 Å was replaced with dextran with a molecular diameter of 270 Å ("Dextran T500," made by Pharmacia Biotech Co., Ltd.). From these values, pore volume PV (51–270) (ml/g) of pores of 51–270 Å with a physiological salt solution was calculated in accordance with the following equation:

$$PV(51-270)=PV(0-270)-PV(0-51).$$

Pore volume PV (0–560) (ml/g) of pores of 0–560 Å with a physiological salt solution was measured in the same way as the above-mentioned, except that the dextran with a molecular diameter of 51 Å was replaced with dextran with a molecular diameter of 560 Å ("Dextran T2000," made by Pharmacia Biotech Co., Ltd.). From these values, pore volume PV (270–560) (ml/g) of pores of 270–560 Å with a physiological salt solution was calculated in accordance with the following equation:

$$PV(270-560)=PV(0-560)-PV(0-270).$$

In addition, the amount of the absorption of the physiological salt solution as to the entirety of the water-swellable crosslinked polymer was defined as PV (0–560).

(b) Size and Size Distribution of Pores in Gels in a State Swollen with Ion-exchanged Water:

About 10 mg (W1 g) of a water-swellable crosslinked polymer is precisely weighed out and then swollen by placing it into a screw tube of 100 ml along with about 30 ml (W4 ml) of ion-exchanged water, and then allowed to stand stationary for 60 hours. About 30 ml (W5 ml) of a 1.00% (Ci %) ion-exchanged water solution of dextran with a molecular diameter of 51 Å ("Dextran T10," made by Pharmacia Biotech Co., Ltd.) is added, and the tube is capped and then shaken for 60 hours with a shaker ("Double Shaker" NR-150, made by Taitec Co., Ltd.). After this shaking, the resultant swollen gel is filtered off with a glass filter. The filtrate is subjected to GPC analysis to determine the concentration (Cf %) of dextran in the filtrate from a calibration curve as made beforehand from the peak height of dextran with a known concentration. Conditions for the GPC analysis are as follows:

GPC analyzer: Shodex GPC System 21, made by Showa Denko Co., Ltd.

Column: "Shodex Asahipak" GF7M-HQ, made by Showa Denko Co., Ltd.

Column temperature: 35° C.

Eluent: $Na_2HPO_4$ (13.8 g), $NaH_2PO_4 \cdot 2H_2O$ (18.46 g), $NaN_3$ (0.04 g), $H_2O$ (1967.7 g)

Flow rate: 0.5 ml/min

Amount of charge: 50 μl

Detector: RI

Pore volume PVW (0–51) (ml/g) of pores of 0–51 Å with ion-exchanged water was calculated from the weights W1, W4, and W5, the initial concentration Ci % of the ion-exchanged water solution of dextran, and the concentration Cf % of dextran in the filtrate in accordance with the following equation:

$$PVW(0-51)(ml/g)=(W4+W5)[1-\{W5/(W4+W5)\}\times(Ci/Cf)]/W1.$$

Pore volumes PVW (0–90), PVW (0–118), PVW (0–270), and PVW (0–560) (ml/g) of pores of 0–90 Å, 0–118 Å, 0–270 Å, and 0–560 Å, respectively, with ion-exchanged water were measured in the same way as the above-mentioned, except that the dextran with a molecular diameter of 51 Å was replaced with four types of dextran with molecular diameters of 90 Å, 118 Å, 270 Å, 560 Å, respectively, ("Dextran T40, T70, T500, T2000," made by Pharmacia Biotech Co., Ltd.). From these values, pore volumes PVW (ml/g) of pores of 51–90 Å, 90–118 Å, 118–270 Å, 270–560 Å, respectively, with ion-exchanged water were calculated in accordance with the following equations:

$$PVW(51-90)=PVW(0-90)-PVW(0-51),$$

$$PVW(90-118)=PVW(0-118)-PVW(0-90),$$

$$PVW(118-270)=PVW(0-270)-PVW(0-118),$$

$$PVW(270-560)=PVW(0-560)-PVW(0-270).$$

(c) Average Pore Size:

The average pore size was calculated from the above-calculated PVW (51–90), PVW (90–118), PVW (118–270), and PVW (270–560) in accordance with the below-mentioned equation, and the standard deviation in pore size was also determined.

---

Average pore size = [25.5 × PVW (0–51 Å)
+70.5 × PVW (51–90 Å)
+104 × PVW (90–118 Å)
+194 × PVW (118–270 Å)
+415 × PVW (270–560 Å)]/
[PVW (0–560 Å)]

---

(d) Evaluation as to Absorbent Articles (kewpie doll test):

Fifty parts by weight of a water-swellable crosslinked polymer and 50 parts by weight of wood-pulverized pulp were mixed together in a dry manner with a mixer. Next, the resultant mixture was shaped into a web of the size of 120 mm×400 mm by pneumatically molding the mixture on a wire screen of 400 mesh (mesh size: 38 μm) with a batch type pneumatic device. In addition, this web was pressed for 5 seconds under a pressure of 2 kg/cm², thus obtaining an absorbent matter of a weight of about 0.047 g/cm².

Next, a back sheet (liquid-unpermeable sheet) of a liquid-unpermeable polypropylene with a so-called leg gather, the above-mentioned absorbent matter, and a top sheet (liquid-permeable sheet) of a liquid-permeable polypropylene were attached to each other in this order with double coated tapes, and two so-called tape fasteners were then provided to the resultant attached product, thus obtaining an absorbent article (i.e. disposable diaper). This absorbent article was fitted up to a so-called kewpie doll (body length: 55 cm, weight: 6 kg), and this doll was laid on its face. Then, a tube was inserted between the absorbent article and the doll, and 50 ml of a physiological salt solution was injected through the tube every 20 minutes to a position corresponding to where a baby boy discharged his urine. This injection operation was ended when the injected physiological salt solution began leaking without being absorbed into the absorbent article, and the amount of the physiological salt solution that had been injected until that time was measured. This kewpie doll test is a test that was carried out correspondingly to circumstances under which the water-absorbent resin was actually used for absorbent articles.

The above-mentioned measurement was repeated four times, and the average of the resultant measurement values was determined and defined as the amount of the absorption.

EXAMPLE 1

Two parts by weight of sodium polyacrylate, which had a viscosity-average molecular weight of 4,000,000 and of which 66 mol % of carboxyl groups were sodium salts, and 1.6 parts by weight of methanol (made by Kanto Chemical Co., Ltd.) were charged into a polypropylene cup and mixed by stirring with a spatula. To the resultant mixture, 4.4 parts by weight of a 9.4 wt % aqueous sodium carbonate solution was added and stirred to adjust the neutralization ratio of the polymer to 75 mol %. Next, 15.2 parts by weight of a 0.07 wt % aqueous solution of ethylene glycol diglycidyl ether ("Denacol" EX-810, made by Nagase Kasei Co., Ltd.) was added and stirred to prepare an aqueous solution with a polymer concentration of 10 wt %. The polypropylene cup was capped so as not to change the solid content concentration due to the evaporation of the water content, and then placed into a dryer ("Convection Oven," made by Sanyo Electric Appliances Co., Ltd.), where the cup was left at 80° C. for 3 hours, thus carrying out a crosslinking reaction. The polypropylene cup was retrieved from the dryer, and the cap was removed from the cup, which was then placed into a vacuum drying oven ("VACUUM DRYING OVEN," made by YAMATO), where the vacuum drying was carried out at 80° C., 20 mmHg for one night. The resultant dried product was pulverized with a portable pulverizer ("Konadon," made by Ishizaki Denki Seisakusho Co., Ltd.) and classified with a sieve to separate a portion that passed through 20 mesh (mesh size: 850 μm), thus obtaining water-absorbent resin (1) according to the present invention. The size distribution of pores of water-absorbent resin (1) in a state swollen with a physiological salt solution is shown in Table 1, which further shows results of the kewpie doll test for an absorbent article as prepared using water-absorbent resin (1). The size distribution of pores of water-absorbent resin (1) in a state swollen with ion-exchanged water is shown in Table 2.

EXAMPLE 2

Two parts by weight of sodium polyacrylate, which had a viscosity-average molecular weight of 3,500,000 and of which 75 mol % of carboxyl groups were sodium salts, was charged into a polypropylene cup, to which 8.0 parts by weight of a 0.13 wt % aqueous solution of ethylene glycol diglycidyl ether ("Denacol" EX-810, made by Nagase Kasei Co., Ltd.) was added and stirred to prepare an aqueous solution with a polymer concentration of 20 wt %. The polypropylene cup was capped so as not to change the solid content concentration due to the evaporation of the water content, and then placed into a dryer ("Convection Oven," made by Sanyo Electric Appliances Co., Ltd.), where the cup was left at 80° C. for 3 hours, thus carrying out a crosslinking reaction. The polypropylene cup was retrieved from the dryer, and the cap was removed from the cup, which was then placed into a vacuum drying oven ("VACUUM DRYING OVEN," made by YAMATO), where the vacuum drying was carried out at 80° C., 20 mmHg for one night. The resultant dried product was pulverized with a portable pulverizer ("Konadon," made by Ishizaki Denki Seisakusho Co., Ltd.) and classified with a sieve to separate a portion that passed through 20 mesh (mesh size: 850 µm), thus obtaining water-absorbent resin (2) according to the present invention. The size distribution of pores of water-absorbent resin (2) in a state swollen with a physiological salt solution is shown in Table 1, which further shows results of the kewpie doll test for an absorbent article as prepared using water-absorbent resin (2).

EXAMPLE 3

Water-absorbent resin (3) according to the present invention was obtained in the same way as of Example 2 except that 8.0 parts by weight of the 0.13 wt % aqueous solution of the Denacol was replaced with 4.67 parts by weight of a 0.21 wt % aqueous solution of the Denacol to prepare an aqueous solution with a polymer concentration of 30 wt %. The size distribution of pores of water-absorbent resin (3) in a state swollen with a physiological salt solution is shown in Table 1, which further shows results of the kewpie doll test for an absorbent article as prepared using water-absorbent resin (3).

EXAMPLE 4

Water-absorbent resin (4) according to the present invention was obtained in the same way as of Example 2 except that 8.0 parts by weight of the 0.13 wt % aqueous solution of the Denacol was replaced with 8.0 parts by weight of a 0.25 wt % aqueous solution of the Denacol to prepare an aqueous solution with a polymer concentration of 20 wt %. The size distribution of pores of water-absorbent resin (4) in a state swollen with a physiological salt solution is shown in Table 1, which further shows results of the kewpie doll test for an absorbent article as prepared using water-absorbent resin (4).

EXAMPLE 5

Two parts by weight of polyacrylic acid with a weight-average molecular weight of 800,000 and 1.6 parts by weight of methanol (made by Kanto Chemical Co., Ltd.) were charged into a polypropylene cup and mixed by stirring with a spatula. To the resultant mixture, 9.7 parts by weight of a 11.3 wt % aqueous sodium carbonate solution was added and stirred to adjust the neutralization ratio of the polymer to 75 mol %. Next, 0.6 parts by weight of a 4.1 wt % aqueous solution of ethylene glycol diglycidyl ether ("Denacol" EX-810, made by Nagase Kasei Co., Ltd.) was added and stirred to prepare an aqueous solution with a polymer concentration of 20 wt %. Thereafter, the same procedure as of Example 1 was carried out, thus obtaining water-absorbent resin (5) according to the present invention. The size distribution of pores of water-absorbent resin (5) in a state swollen with a physiological salt solution is shown in Table 1, which further shows results of the kewpie doll test for an absorbent article as prepared using water-absorbent resin (5).

COMPARATIVE EXAMPLE 1

A reaction solution was prepared by dissolving 3.59 parts by weight of trimethylolpropane triacrylate as an internal crosslinking agent into 5,500 parts by weight of a 39 wt % aqueous solution of sodium acrylate with a neutralization ratio of 75 mol %. Next, this solution was degassed under a nitrogen gas atmosphere for 30 minutes, and then supplied into a reaction vessel as prepared by capping a stainless-steel-made double arm type kneader having two sigma type wings and a jacket. While maintaining the reaction solution at 30° C., the atmosphere inside the system was replaced with a nitrogen gas. Next, while stirring the reaction solution, 3.4 parts by weight of ammonium persulfate and 0.016 parts by weight of L-ascorbic acid were added as initiators, so that a polymerization reaction got started about 1 minute after. The polymerization was carried out at 30–80° C., and the reaction was ended after 60 minutes from the initiation of the polymerization. The resultant hydrogel polymer was spread on a 50-mesh metal net and dried at 150° C. with hot air for 90 minutes. Then, the resultant dried product was pulverized with a portable pulverizer ("Konadon," made by Ishizaki Denki Seisakusho Co., Ltd.) and classified with a sieve to separate a portion that passed through 20 mesh (mesh size: 850 µm), thus obtaining comparative water-absorbent resin (1). The size distribution of pores of comparative water-absorbent resin (1) in a state swollen with a physiological salt solution is shown in Table 1, which further shows results of the kewpie doll test for an absorbent article as prepared using comparative water-absorbent resin (1).

COMPARATIVE EXAMPLE 2

Comparative water-absorbent resin (2) was obtained in the same way as of Comparative Example 1 except that the dissolution of 3.59 parts by weight of trimethylolpropane triacrylate as an internal crosslinking agent into 5,500 parts by weight of the 39 wt % aqueous solution of sodium acrylate with a neutralization ratio of 75 mol % was replaced with the dissolution of 2.39 parts by weight of trimethylolpropane triacrylate as an internal crosslinking agent into 5,500 parts by weight of a 33 wt % aqueous solution of sodium acrylate with a neutralization ratio of 75 mol %. The size distribution of pores of comparative water-absorbent resin (2) in a state swollen with a physiological salt solution is shown in Table 1, which further shows results of the kewpie doll test for an absorbent article as prepared using comparative water-absorbent resin (2).

EXAMPLE 6

A reaction solution was prepared by charging 72 g of acrylic acid, 0.536 g of polyethylene glycol as the internal crosslinking agent, and 288 g of ion-exchanged water as the solvent into a polypropylene cup of 1 liter. Next, while maintaining the temperature of this reaction solution at 15° C., the internal atmosphere of the reaction vessel was replaced with a nitrogen gas. Then, 2.16 g of a 10 wt % aqueous 2,2'-azobis(2-amidinopropane) dihydrochloride solution, 3.6 g of a 1 wt % aqueous L-ascorbic acid solution, and 4.26 g of a 3.5 wt % aqueous hydrogen peroxide solution were added as polymerization initiators to the reaction solution to initiate a polymerization reaction. After the temperature of the reaction solution had reached the maximum temperature, the temperature of the jacket was controlled to maintain the temperature of the reaction solution at 55° C., thus aging the reaction solution for 10 hours. After the reaction had ended, the resultant hydrogel crosslinked polymer was pulverized into particles of 1–2 mm with scissors, thus obtaining particles of hydrogel crosslinked polymer (A).

Next, hydrogel crosslinked polymer (A) was maintained at about 50° C., to which 79.5 g of sodium carbonate as the neutralizing agent and 82.5 g of ion-exchanged water were added to mix them, and the resultant mixture was maintained at room temperature for 24 hours.

Then, the neutralized polymer was dried with hot air of 50° C. for 16 hours, and the resultant dried product was pulverized with a vibration mill, thus obtaining water-absorbent resin (6).

Results of the kewpie doll test for an absorbent article as prepared using water-absorbent resin (6) are shown in Table 2, which further shows the size distribution of pores of water-absorbent resin (6) in a state swollen with ion-exchanged water.

EXAMPLE 7

Water-absorbent resin (7) was obtained by: adding 0.5 parts by weight of propylene glycol as a first surface-crosslinking agent, 0.05 parts by weight of ethylene glycol diglycidyl ether as a second surface-crosslinking agent, and an aqueous solution, comprising 3 parts by weight of water and 0.75 parts by weight of isopropyl alcohol as the hydrophilic organic solvent, to 100 parts by weight of water-absorbent resin (6) as obtained in Example 6; mixing them; and heating the resultant mixture at 175° C. for 60 minutes.

Results of the kewpie doll test for an absorbent article as prepared using water-absorbent resin (7) are shown in Table 2, which further shows the size distribution of pores of water-absorbent resin (7) in a state swollen with ion-exchanged water.

COMPARATIVE EXAMPLE 3

A reaction solution, as prepared by dissolving 2.87 g of polyethylene glycol diacrylate as another monomer into 5,367 g of a 33 wt % aqueous solution of partially neutralized sodium acrylate with a neutralization ratio of 75 mol %, was charged into a reaction vessel as prepared by capping a stainless-steel-made double arm type kneader of a capacity of 10 liters having two sigma type wings and a jacket. Next, while maintaining the temperature of this reaction solution at 26° C., the internal atmosphere of the reaction vessel was replaced with a nitrogen gas. Then, while stirring a blade of the above-mentioned kneader, 12 g of a 20 wt % aqueous sodium persulfate solution and 10 g of a 1 wt % aqueous L-ascorbic acid solution were added as polymerization initiators to the reaction solution, and a polymerization reaction was carried out while pulverizing the resultant gel for 60 minutes. As a result, hydrogel crosslinked polymer (B) was obtained in the form of particles.

Then, polymer (B) was dried at 160° C. with hot air for 65 minutes and then pulverized, thus obtaining comparative water-absorbent resin (3).

Results of the kewpie doll test for an absorbent article as prepared using comparative water-absorbent resin (3) are shown in Table 2, which further shows the size distribution of pores of comparative water-absorbent resin (3) in a state swollen with ion-exchanged water.

COMPARATIVE EXAMPLE 4

Comparative water-absorbent resin (4) was obtained by carrying out a surface-crosslinking treatment using comparative water-absorbent resin (3) in the same way as of Example 7.

Results of the kewpie doll test for an absorbent article as prepared using comparative water-absorbent resin (4) are shown in Table 2, which further shows the size distribution of pores of comparative water-absorbent resin (4) in a state swollen with ion-exchanged water.

COMPARATIVE EXAMPLE 5

A reaction solution, as prepared by dissolving 2.87 g of polyethylene glycol diacrylate as another monomer into 5,757 g of a 30 wt % aqueous solution of partially neutralized sodium acrylate with a neutralization ratio of 65 mol %, was charged into a reaction vessel as prepared by capping a stainless-steel-made double arm type kneader of a capacity of 10 liters having two sigma type wings and a jacket. Next, while maintaining the temperature of this reaction solution at 26° C., the internal atmosphere of the reaction vessel was replaced with a nitrogen gas. Then, while stirring a blade of the above-mentioned kneader, 12 g of a 20 wt % aqueous sodium persulfate solution and 10 g of a 1 wt % aqueous L-ascorbic acid solution were added as polymerization initiators to the reaction solution, and a polymerization reaction was carried out while pulverizing the resultant gel for 60 minutes. As a result, hydrogel crosslinked polymer (C) was obtained in the form of particles.

Then, polymer (C) was dried at 160° C. with hot air for 65 minutes and then pulverized, thus obtaining comparative water-absorbent resin (5).

Results of the kewpie doll test for an absorbent article as prepared using comparative water-absorbent resin (5) are shown in Table 2, which further shows the size distribution of pores of comparative water-absorbent resin (5) in a state swollen with ion-exchanged water.

COMPARATIVE EXAMPLE 6

Comparative water-absorbent resin (6) was obtained by carrying out a surface-crosslinking treatment using comparative water-absorbent resin (5) in the same way as of Example 7.

Results of the kewpie doll test for an absorbent article as prepared using comparative water-absorbent resin (6) are shown in Table 2, which further shows the size distribution of pores of comparative water-absorbent resin (6) in a state swollen with ion-exchanged water.

TABLE 1

|  | Reaction conditions | | | Size distribution of pores in state swollen with physiological salt solution | | | Amount of liquid as absorbed till |
|---|---|---|---|---|---|---|---|
|  | Molecular weight of prepolymer | Concentration of prepolymer [wt %] | Amount of EGDGE* added [wt %] | 0–51 Å [ml/g]([%]) | 51–270 Å [ml/g]([%]) | 270–560 Å [ml/g]([%]) | leaking in kewpie test [ml] |
| Example 1 | 4,000,000 | 10 | 0.5 | 0.1 (0.2) | 59.2 (89.1) | 7.1 (10.7) | 270 |
| Example 2 | 3,500,000 | 20 | 0.5 | 2.7 (6.0) | 30.1 (67.0) | 12.3 (27.0) | 260 |
| Example 3 | 3,500,000 | 30 | 0.5 | 2.0 (4.0) | 39.4 (77.1) | 9.7 (18.9) | 260 |
| Example 4 | 3,500,000 | 20 | 1.0 | 6.1 (15.4) | 23.9 (61.0) | 9.5 (23.6) | 250 |
| Example 5 | 800,000 | 20 | 1.0 | 0.2 (0.4) | 43.0 (76.6) | 12.9 (23.0) | 250 |

TABLE 1-continued

| | Reaction conditions | | | Size distribution of pores in state swollen with physiological salt solution | | | Amount of liquid as absorbed till leaking in kewpie test [ml] |
|---|---|---|---|---|---|---|---|
| | Molecular weight of prepolymer | Concentration of prepolymer [wt %] | Amount of EGDGE* added [wt %] | 0–51 Å [ml/g]([%]) | 51–270 Å [ml/g]([%]) | 270–560 Å [ml/g]([%]) | |
| Comparative Example 1 | — | 39** | 0.17*** | 0.5 (1.3) | 22.0 (56.7) | 16.3 (42.0) | 210 |
| Comparative Example 2 | — | 33** | 0.13*** | 0.3 (0.5) | 28.5 (51.0) | 27.1 (48.5) | 210 |

*: Ethylene glycol diglycidyl ether
**: Monomer concentration
***: Trimethylolpropane triacrylate As is clear from Table 1, it would be understood that there is a great difference between the amounts of the liquid as absorbed till leaking in the kewpie test when PV (51–270) is less than 60% and when PV (51–270) is not less than 60%, and that 60% is the critical value. In addition, it would be understood that when PV (51–270) is not less than 80%, the absorption capacity is further improved.

TABLE 2

| | 0–51 Å [ml/g]([%]) | 51–90 Å [ml/g]([%]) | 90–118 Å [ml/g]([%]) | 118–270 Å [ml/g]([%]) | 270–560 Å [ml/g]([%]) | Amount of liquid as absorbed till leaking in kewpie test [ml] | 51–270 Å [%] | Average pore size (Å) | Standard deviation in pore size |
|---|---|---|---|---|---|---|---|---|---|
| Example 1 | 10.4 (1.0) | 114.3 (11.0) | 343.0 (33.0) | 447.0 (43.0) | 124.7 (12.0) | 270 | 87.0 | 172.8 | 98.9 |
| Example 6 | 1.4 (0.2) | 154.1 (21.7) | 32.5 (4.6) | 393.0 (55.3) | 129.8 (18.2) | 260 | 81.6 | 203.4 | 114.5 |
| Example 7 | 16.9 (3.2) | 148.2 (25.1) | 212.5 (12.3) | 252.4 (48.4) | ? (11.0) | 270 | 85.8 | 170.8 | 102.8 |
| Comparative Example 3 | 7.3 (2.9) | 92.2 (36.7) | 14.2 (5.7) | 83.4 (33.2) | 54.0 (21.5) | 210 | 75.6 | 186.2 | 131.6 |
| Comparative Example 4 | 13.6 (3.0) | 125.7 (27.7) | 24.4 (5.4) | 152.4 (33.5) | 138.1 (30.4) | 210 | 66.6 | 174.1 | 140.8 |
| Comparative Example 5 | 21.8 (9.0) | 76.6 (31.7) | 25.6 (10.6) | 69.5 (28.8) | 48.2 (19.9) | 210 | 71.1 | 217.1 | 132.6 |
| Comparative Example 6 | 37.8 (9.3) | 53.8 (13.2) | 153.5 (15.2) | 184.7 (45.3) | 69.4 (17.0) | 210 | 73.7 | 185.9 | 118.8 |

As is clear from Table 2, it would be understood that there is a great difference between the amounts of the liquid as absorbed till leaking in the kewpie test when PVW (51–270) is less than 80% and when PVW (51–270) is not less than 80%, and that 80% is the critical value. In addition, it would be understood that there is a great difference between the amounts of the liquid as absorbed till leaking in the kewpie test when the standard deviation in pore size is more than 115 and when the standard deviation in pore size is less than 115 with regard to the water-absorbent resins with an average pore size of 100 to 300 Å, and that a standard deviation of 115 in pore size is the critical value. Furthermore, it would be understood that when PVW (51–270) is 85% or more or when the standard deviation in pore size is 110 or less, and further, 105 or less, the absorption capacity is further improved.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A water-swellable crosslinked polymer that has a base volume of 100 v/v % for the absorption of a physiological salt solution, wherein the water-swellable crosslinked polymer comprises pores having a diameter of 51–270 Å when the polymer is swollen with the physiological salt solution to form a gel, and wherein said pores having said diameter have a total pore volume of 60 v/v % or more when the polymer is swollen with the physiological salt solution to form a gel.

2. A water-swellable crosslinked polymer that has a base volume of 100 v/v % for the absorption of a physiological salt solution, wherein the water-swellable crosslinked polymer comprises pores having a diameter of 51–270 Å when the polymer is swollen with the physiological salt solution to form a gel, and wherein said pores having said diameter have a total pore volume of 60 v/v % or more when the polymer is swollen with the physiological solution to form a gel (and defining said total pore volume as PV (51–270 Å)), wherein PV (51–270 Å) is defined by a method comprising the steps of:

A. allowing a water-swellable crosslinked polymer (W1 g), which stands in an equilibrium state swollen with a physiological salt solution (W2 ml), to fall again into an equilibrium state by adding a physiological salt solution (W3 ml, concentration Ci %) of a thread-ball-shaped molecule with molecular diameter R to the polymer; and then filtering off the polymer as swollen with the physiological salt solution; and then measuring concentration Cf % of the thread-ball-shaped molecule in the resultant filtrate;

B. defining PV (0–R) (ml/g) as PV (0–R) (ml/g)=(W2+W3)[1−{W3/(W2+W3)} ×(Ci/Cf)]/W1;

C. determining PV (0–51 Å) and PV (0–270 Å) using a thread-ball-shaped molecule with R of 51 Å and a thread-ball-shaped molecule with R of 270 Å; and D. defining PV (51–270 Å) as PV (51–270 Å)=PV (0–270 Å)−PV (0–51 Å).

3. A water-swellable crosslinked polymer that has a base volume of 100 v/v % for the absorption of an ion-exchanged water, wherein the water-swellable crosslinked polymer comprises pores having a diameter of 51–270 Å when the polymer is swollen with the ion exchanged water to form a gel, and wherein said pores having said diameter have a total pore volume of 80 v/v % or more when the polymer is swollen with the ion-exchanged water to form a gel.

4. A water-swellable crosslinked polymer that has a base volume of 100 v/v % for the absorption of an ion-exchanged water, wherein the water-swellable crosslinked polymer comprises pores having a diameter of 51–270 Å when the polymer is swollen with the ion exchanged water to form a gel, and wherein said pores having said diameter have a total pore volume of 80 v/v % or more when the polymer is swollen with the ion-exchanged water to form a gel (and defining said total pore volume as PVW (51–270 Å)), wherein PVW (51–270 Å) is defined by a method comprising the steps of:

E. allowing a water-swellable crosslinked polymer (W1 g), which stands in an equilibrium state swollen with ion-exchanged water (W4 ml), to fall again into an equilibrium state by adding an ion-exchanged water (W5 ml, concentration Ci %) of a thread-ball-shaped molecule with molecular diameter R to the polymer; and then filtering off the polymer as swollen with the ion-exchanged water; and then measuring concentration Cf % of the thread-ball-shaped molecule in the resultant filtrate;

F. defining PVW (0–R) (ml/g) as PVW (0–R) (ml/g)=(W4+W5)[1−{W5/(W4+W5)} ×(Ci/Cf)]/W1;

G. determining PVW (0–51 Å) and PVW (0–270 Å) using a thread-ball-shaped molecule with R of 51 Å and a thread-ball-shaped molecule with R of 270 Å; and H. defining PVW (51–270 Å) as PVW (51–270 Å)=PVW (0–270 Å)−PVW (0–51 Å).

5. A water-swellable crosslinked polymer that absorbs an ion-exchanged water, wherein the water-swellable crosslinked polymer comprises pores, wherein said pores have an average pore size of 100–300 Å with a standard deviation of 115 or less when the polymer is swollen with the ion exchanged water to form a gel.

6. A water-swellable crosslinked polymer that absorbs an ion-exchanged water wherein the water-swellable crosslinked polymer comprises pores, wherein said pores have an average pore size of 100–300 Å with a standard deviation of 115 or less when the polymer is swollen with the ion exchanged water to form a gel, wherein the average pore size is defined by a method comprising the steps of:

I. allowing a water-swellable crosslinked polymer (W1 g), which stands in an equilibrium state swollen with ion-exchanged water (W4 ml), to fall again into an equilibrium state by adding an ion-exchanged water (W5 ml, concentration Ci %) of a thread-ball-shaped molecule with molecular diameter R to the polymer; and then filtering off the polymer as swollen with the ion-exchanged water; and then measuring concentration Cf % of the thread-ball-shaped molecule in the resultant filtrate;

J. defining PVW (0–R) (ml/g) as PVW (0–R) (ml/g)= (W4+W5)[1−{W5/(W4+W5)} ×(Ci/Cf)]/W1;

K. determining PVW (0–51 Å), PVW (51–90 Å), PVW (90–118 Å), PVW (118–270 Å), PVW (270–560 Å), and PVW (0–560 Å) using a thread-ball-shaped molecule with R of 51 Å, a thread-ball shaped molecule with R of 90 Å, a thread-ball-shaped molecule with R of 118 Å, a thread-ball-shaped molecule with R of 270 Å, and a thread-ball-shaped molecule with R of 560 Å; and L. defining the average pore size as:

$$\text{average pore size} = [25.5 \times \text{PVW (0–51 Å)} \\ + 70.5 \times \text{PVW (51–90 Å)} \\ + 104 \times \text{PVW (90–118 Å)} \\ + 194 \times \text{PVW (118–270 Å)} \\ + 415 \times \text{PVW (270–560 Å)}]/ \\ [\text{PVW (0–560 Å)}]$$

7. The water-swellable crosslinked polymer according to claim 1, wherein the water swellable crosslinked polymer is a crosslinked product of partially neutralized polyacrylic acids.

8. The water-swellable crosslinked polymer according to claim 2, wherein the water swellable crosslinked polymer is a crosslinked product of partially neutralized polyacrylic acids.

9. The water-swellable crosslinked polymer according to claim 3, wherein the water swellable crosslinked polymer is a crosslinked product of partially neutralized polyacrylic acids.

10. The water-swellable crosslinked polymer according to claim 4, wherein the water swellable crosslinked polymer is a crosslinked product of partially neutralized polyacrylic acids.

11. The water-swellable crosslinked polymer according to claim 5, wherein the water swellable crosslinked polymer is a crosslinked product of partially neutralized polyacrylic acids.

12. The water-swellable crosslinked polymer according to claim 6, wherein the water swellable crosslinked polymer is a crosslinked product of partially neutralized polyacrylic acids.

13. The water-swellable crosslinked polymer according to claim 1, wherein the water swellable crosslinked polymer is a substantially nonfoamed crosslinked product.

14. The water-swellable crosslinked polymer according to claim 2, wherein the water swellable crosslinked polymer is a substantially nonfoamed crosslinked product.

15. The water-swellable crosslinked polymer according to claim 3, wherein the water swellable crosslinked polymer is a substantially nonfoamed crosslinked product.

16. The water-swellable crosslinked polymer according to claim 4, wherein the water swellable crosslinked polymer is a substantially nonfoamed crosslinked product.

17. The water-swellable crosslinked polymer according to claim 5, wherein the water swellable crosslinked polymer is a substantially nonfoamed crosslinked product.

18. The water-swellable crosslinked polymer according to claim 6, wherein the water swellable crosslinked polymer is a substantially nonfoamed crosslinked product.

* * * * *